United States Patent
Gaiselmann et al.

(10) Patent No.: US 10,426,496 B2
(45) Date of Patent: Oct. 1, 2019

(54) METHOD FOR SURGICALLY REMOVING A TUMOR FROM A WOMAN'S BREAST

(71) Applicants: Thomas Gaiselmann, Villingendorf (DE); Karl-Heinz Bachmann, Villingendorf (DE); Siegfried Riek, Rottweil (DE)

(72) Inventors: Thomas Gaiselmann, Villingendorf (DE); Karl-Heinz Bachmann, Villingendorf (DE); Siegfried Riek, Rottweil (DE)

( * ) Notice: Subject to any disclaimer, the term of this patent is extended or adjusted under 35 U.S.C. 154(b) by 95 days.

(21) Appl. No.: 14/331,960

(22) Filed: Jul. 15, 2014

(65) Prior Publication Data

US 2015/0051495 A1    Feb. 19, 2015

(30) Foreign Application Priority Data

Aug. 15, 2013  (DE) .................. 10 2013 216 235

(51) Int. Cl.
| | |
|---|---|
| *A61B 5/00* | (2006.01) |
| *A61B 17/22* | (2006.01) |
| *A61B 17/32* | (2006.01) |
| *A61B 17/34* | (2006.01) |
| *A61B 8/12* | (2006.01) |

(Continued)

(52) U.S. Cl.
CPC ............ *A61B 17/22* (2013.01); *A61B 8/12* (2013.01); *A61B 17/32002* (2013.01); *A61B 17/3421* (2013.01); *A61B 17/3478* (2013.01); *A61B 8/0841* (2013.01); *A61B 17/3474* (2013.01); *A61B 90/361* (2016.02); *A61B 2017/008* (2013.01); *A61B 2017/0034* (2013.01); *A61B 2017/00261* (2013.01); *A61B 2017/00796* (2013.01); *A61B 2017/00907* (2013.01);

(Continued)

(58) Field of Classification Search
CPC .... A61B 2017/3454; A61B 17/320016; A61B 17/3474; A61B 1/00135; A61B 2018/00333; A61B 17/3421; A61B 17/3478; A61B 2017/008; A61B 2017/00796
See application file for complete search history.

(56) References Cited

U.S. PATENT DOCUMENTS 5,743,881 A * 4/1998 Demco ............. A61M 25/0606
                                                    604/158
7,384,423 B1 * 6/2008 Chin ................ A61B 17/00008
                                                    606/190

(Continued)

FOREIGN PATENT DOCUMENTS

| WO | 2013/000536 A1 | 1/2013 |
| WO | 2013/000540 A1 | 1/2013 |

*Primary Examiner* — Joel Lamprecht
(74) *Attorney, Agent, or Firm* — Akerman LLP; Peter A. Chiabotti

(57) ABSTRACT

A method for surgically removing a tumor from a woman's breast is provided. The method can include inserting an optical trocar having a working channel and a transparent tip through a skin incision, guiding the transparent tip of the trocar through breast tissue with visualization such that the transparent tip of the trocar is placed adjacent to the tumor, insufflating gas via the working channel of the trocar to create a cavity in an operative field next to the tumor, dissecting the tumor free with a surgical instrument inserted through the working channel and removing the tumor through the trocar.

10 Claims, 3 Drawing Sheets

(51) Int. Cl.
 *A61B 17/00* (2006.01)
 *A61B 8/08* (2006.01)
 *A61B 90/00* (2016.01)

(52) U.S. Cl.
 CPC ............... *A61B 2017/22072* (2013.01); *A61B 2017/320024* (2013.01); *A61B 2017/3445* (2013.01)

(56) References Cited

U.S. PATENT DOCUMENTS

| | | | | |
|---|---|---|---|---|
| 2002/0176849 | A1* | 11/2002 | Slepian | A61K 9/0024 424/93.7 |
| 2004/0199159 | A1* | 10/2004 | Lee | A61B 8/0825 606/47 |
| 2004/0204671 | A1* | 10/2004 | Stubbs | A61B 17/3421 604/26 |
| 2005/0288622 | A1* | 12/2005 | Albrecht | A61B 17/3417 604/23 |
| 2007/0129719 | A1* | 6/2007 | Kendale | A61B 1/00096 606/41 |
| 2011/0098531 | A1* | 4/2011 | To | A61B 17/0218 600/114 |
| 2013/0274786 | A1* | 10/2013 | Chin | A61B 17/00008 606/190 |
| 2013/0331731 | A1* | 12/2013 | Taylor | A61B 1/0008 600/560 |
| 2014/0039491 | A1* | 2/2014 | Bakos | A61B 18/1492 606/41 |

\* cited by examiner

METHOD FOR SURGICALLY REMOVING A TUMOR FROM A WOMAN'S BREAST

CROSS REFERENCE TO RELATED APPLICATIONS

This application claims priority to German Patent Application No. DE 10 2013 216 235.9 filed Aug. 15, 2013, which is hereby incorporated by reference in its entirety.

BACKGROUND

The application relates to a method for surgically removing a tumor from a woman's breast.

As a rule, tumors in the glandular and fatty tissue of the female breast are removed in that an incision is made in the breast above the tumor. As a rule this is unavoidable with malignant tumors. In the case of benign tumors, such as for instance fibroadenomas, which are common, such a surgical incision in the breast is undesirable, especially with respect to the cosmetically disadvantageous scar formation. In accordance with the prior art, benign tumors such as e.g. fibroadenomas up to a size of approx. 20 mm may be removed using vacuum-assisted biopsy. Since it is not possible to control bleeding with this method and work is performed from outside using ultrasound imaging, visualization of the operative field is limited when there is bleeding so that frequently complete removal is not possible and parts of the tumor are left behind and must then be removed at a later time in another procedure.

SUMMARY

The underlying object of the disclosure is to develop a surgical method that permits minimally invasive removal of a tumor from a woman's breast.

This object is attained using a method having the features and structures recited herein. This may be accomplished in particular with direct visualization using classic endoscopic surgical techniques such as dissection, hemostasis, and tissue removal. Instruments of coagulation or cryosurgery or ultrasound dissectors, clamp devices, or morcellators, for instance, may be used for this.

The disclosed surgical technique uses a so-called optical trocar for minimally invasive laparoscopy. Such trocars are described for instance in WO 2013/000536 A1 and WO 2013/000540 A1. Such an optical trocar has a transparent conical tip through which the tissue positioned just outside the tip may be visualized by means of an optical unit inserted into the trocar when the trocar tip penetrates the tissue. The trocar has axially continuous working channels through which surgical micro-instruments may be passed. The distal working ends of the micro-instruments may emerge distally at the tip of the trocar in order to perform surgical steps, for which purpose the micro-instruments are actuated by means of proximal handles that remain disposed extracorporeally at the proximal end of the trocar.

A continuous longitudinal working space may be embodied as an insufflation channel through which gas, especially $CO_2$, may be insufflated into the abdomen when the trocar tip has penetrated into the abdomen. In particular one or a plurality of the working channels may also be used as insufflation channels.

The working channels and where applicable the insufflation channel may be embodied in the wall of the trocar. If the trocar comprises a trocar member and a trocar sleeve that encloses the latter, the working channels and where applicable the insufflation channel are preferably embodied in the trocar sleeve. However, insufflation may also be performed via the space between the trocar member and the trocar sleeve. In the known laparoscopic surgical technique, while visualizing through the transparent tip, the trocar is advanced through the abdominal wall until the tip reaches the natural abdominal cavity, into which the gas may be insufflated.

In contrast to this known laparoscopic surgical technique, in accordance with the disclosure, a tumor that is embedded in the surrounding breast tissue and is completely enclosed thereby is removed. Thus there is no natural body cavity into which the trocar may be advanced in order then to visually orient the trocar to the desired operative field in the cavity.

In accordance with the disclosure, therefore, the optical trocar is inserted into the breast tissue through a small incision in the skin and is guided through the breast tissue to the tumor that is to be removed. The transparent tip of the optical trocar initially permits visualization only of the tissue that is adjacent to the trocar tip during its penetration and along which the trocar tip moves. It is only when the trocar tip is placed in the area of the tumor that is to be removed that this tumor becomes visible through the transparent trocar tip by means of the optical unit.

As soon as the tip of the trocar is placed against the tumor, gas is insufflated via one of the working channels, which channel is in particular embodied as an insufflation channel, in order to press the soft breast tissue away and thus to create an artificial cavity. The micro-surgical instruments may then be moved out of the distal trocar tip into this artificial cavity to dissect the tumor and free it from the surrounding breast tissue.

The tumor may then be removed through the trocar, for instance also via one of the working channels and in particular through the trocar sleeve. Depending on the size of the tumor, it may be removed completely or will have to be morcellated.

Techniques that are known per se may be used to place the tip of the trocar next to the tumor that is to be removed. It is possible to localize the tumor using a wire marking (U.S. Pat. No. 5,221,269) which then may be sighted when the trocar enters. It is also possible to visualize the tumor and the penetrating trocar by means of ultrasound.

To facilitate insufflation and creation of an operative cavity next to the tumor that is to be removed, after placing the trocar tip, it may be advantageous initially to insert a dilatation balloon through a working channel to first dissect the tissue for gas insufflation.

Only a small incision in the skin is necessary for introducing the trocar so that the cosmetic damage is slight. It is best when the incision in the skin is a periareolar incision so that the scar that remains is practically invisible.

Another advantage of the disclosed method results from the fact that coagulation instruments may also be inserted via the working channels in order to coagulate the injured blood vessels. In addition, small blood vessels are closed simply by the pressure of the insufflated gas. Because of this, there is only minor bleeding during the procedure so that the view of the operative field is hardly affected with respect to dissecting the tumor.

The disclosure shall be explained in greater detail in the following using an exemplary embodiment depicted in the drawings.

DETAILED DESCRIPTION OF THE ILLUSTRATED EMBODIMENTS

Figure 1:
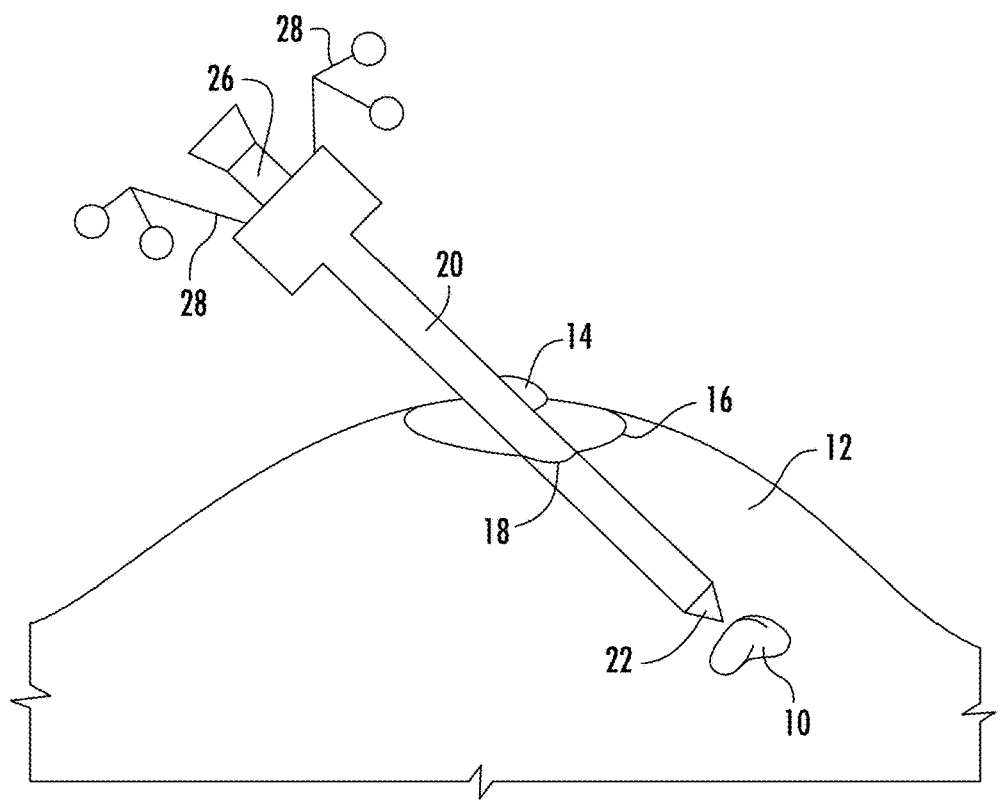
FIG. 1 depicts the trocar being inserted through an incision in the skin and the trocar tip being placed next to a tumor that is to be removed.

The inventive method is used for minimally invasive removal of a tumor 10, for instance a fibroadenoma, from the tissue of a woman's breast (Mamma) 12. To this end, first a small incision 18 is made in the skin, preferably on the edge 16 of the areola 14. An optical trocar 20 is inserted through the skin incision 18. The position of the tumor 10 is visualized for example by means of a wire marking or by means of ultrasound so that the tip of the trocar may be guided towards the operative field of the tumor 10 that is to be removed.

The trocar 20 is embodied as an optical trocar and has a transparent tip 22. Through this tip 22 it is possible to visualize the tissue adjacent to the tip 22 and the advance of the tip 22 through this tissue by means of an optical unit 26 inserted into the trocar 20.

The trocar 20 preferably comprises an inner trocar member with the transparent conical tip 22 and a trocar sleeve 24 that encloses this trocar member. Working channels are embodied longitudinally in the trocar 20. At least one of the working channels is also used, at least at times, as an insufflation channel. In one embodiment, one of the working channels is embodied as an insufflation channel. If the trocar 20 comprises only one trocar member, then the working channels and where applicable the insufflation channel are embodied in the wall surrounding the optical unit 26. If the trocar 20 comprises a trocar member and a trocar sleeve 24, then the working channels and where applicable the insufflation channel are preferably embodied in the trocar sleeve 24 or in the space between the trocar member and the trocar sleeve 24. The working channels and where applicable the insufflation channel exit distally at the tip 22, while at the proximal end of the trocar 20 the insufflation channel may be closed via a valve (not shown) on a gas supply. The working channels terminate proximally in input openings via which surgical micro-instruments 28 may be inserted while sealed.

Figure 2:
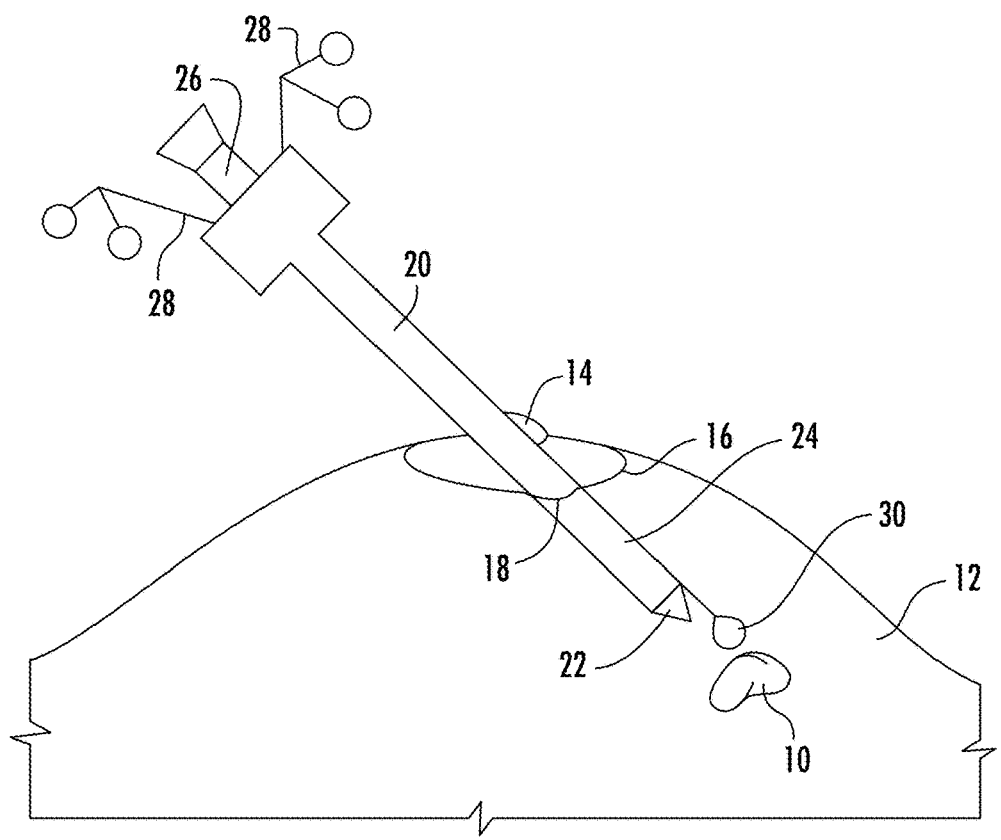
FIG. 2 depicts the creation of an initial artificial cavity by means of a dilatation balloon.

As soon as the tip 22 of the trocar 20 has been placed next to the tumor 10, as is depicted in FIG. 1, preferably a dilatation balloon 30 is inserted through one of the working channels and emerges at the distal tip 22 such that it is disposed immediately adjacent to the tumor 10, as is depicted in FIG. 2. The dilatation balloon 30 is inflated so that it dissects the tissue surrounding the tumor 10 and creates an artificial cavity.

Figure 3:
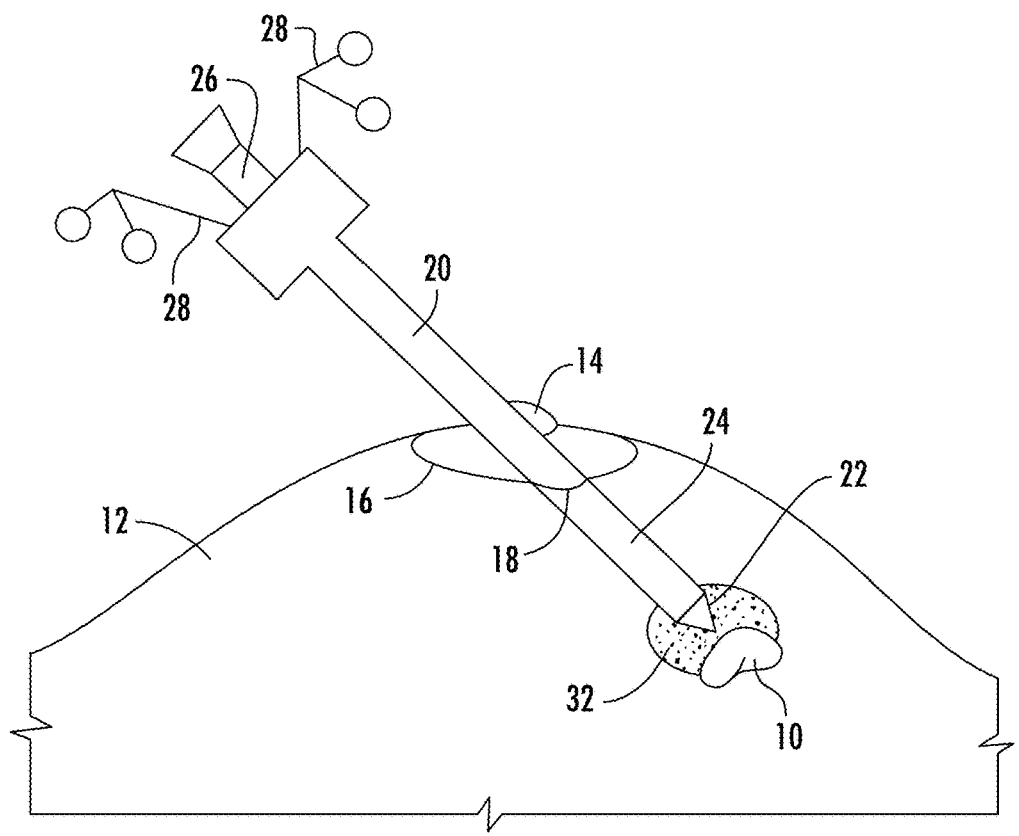
FIG. 3 depicts the insufflation of a gas into this initial cavity.

Then gas, typically $CO_2$, is insufflated via the insufflation channel. The insufflation gas that exits under pressure at the tip 22 of the trocar 20 expands the artificially created cavity 32, as FIG. 3 depicts.

Figure 4:
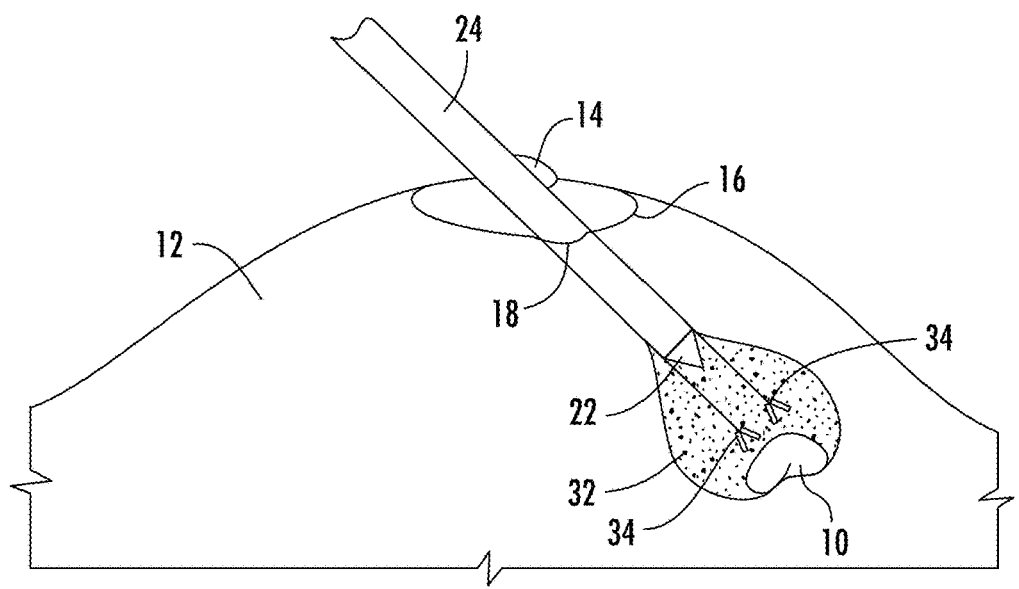
FIG. 4 depicts the dissection of the tumor with visualization by means of surgical micro-instruments.

During further insufflation, the cavity 32 expands further, as FIG. 4 depicts, so that the tumor is accessible. The distal working ends 34 of the micro-instruments 28 may now be moved distally out of the tip 22 of the trocar 20 in order to dissect the tumor 10 free; the micro-instruments 28 are actuated using their extra-corporeal handles. The tumor 10 is dissected while being visualized through the transparent tip 22 by means of the optical unit 26.

Alternatively, if the trocar 20 comprises a trocar member and a trocar sleeve 24, the trocar member may be withdrawn from the trocar sleeve 24 and replaced by an endoscope optical unit that is used to visualize the dissection.

Figure 5:
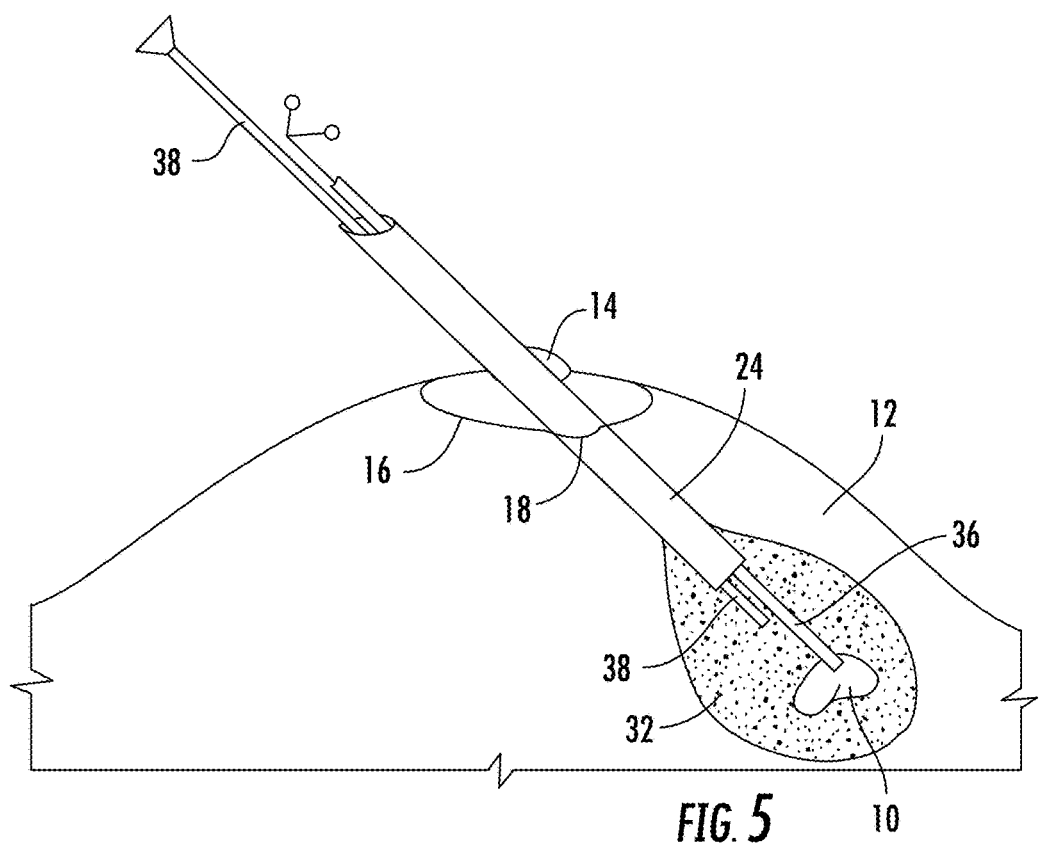
FIG. 5 depicts the morcellation of the tumor with visualization.

As soon as the tumor has been dissected free, as FIG. 5 illustrates, the tumor 10 is retrieved through the trocar 20; for this purpose the trocar member is withdrawn so that the inner channel of the trocar sleeve 24 is free. If the tumor 10 is so large that it cannot be removed intact through the trocar 20, a morcellator 36 may be inserted through the trocar 24 sleeve and may be used to break up the tumor 10. A visualization optics unit 38 may be inserted through one of the working channels to perform the morcellation with visualization.

Figure 6:
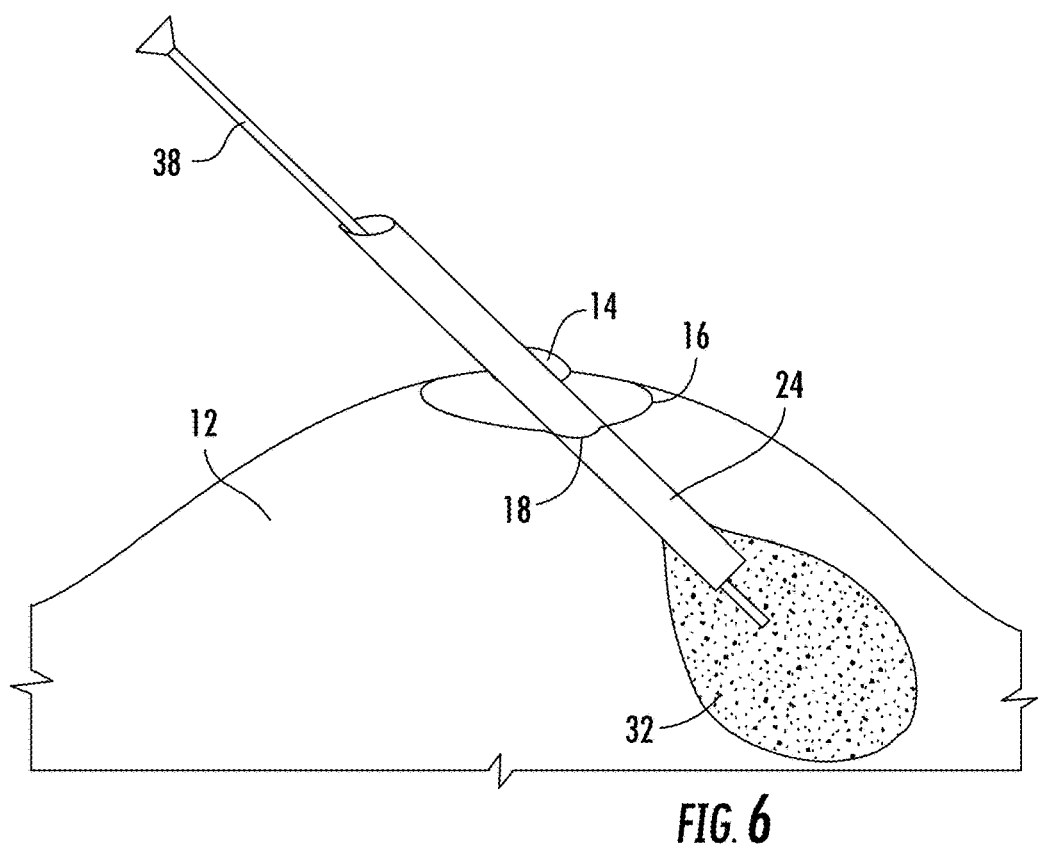
FIG. 6 depicts the operative field after the tumor has been removed and before the insufflation gas has been released.

FIG. 6 depicts the situation after the tumor 10 has been completely removed. The cavity 32 is still filled with the insufflation gas. The insufflation gas is then let out via the trocar 20 so that the cavity 32 and thus the operative wound can close.

REFERENCE NUMBERS

10 Tumor
12 Breast (Mamma)
14 Areola
16 Edge of areola
18 Skin incision
20 Trocar
22 Tip
24 Trocar sleeve
26 Optical unit
28 Micro-instruments
30 Dilatation balloon
32 Cavity
34 Working end
36 Morcellator
38 Visualization optical unit

What is claimed:

1. A method for surgically removing a tumor from a woman's breast, comprising:
    inserting a single optical trocar having working channels and a transparent tip through a skin incision located at a breast;
    visually guiding the transparent tip of the single optical trocar as the single optical trocar advances through breast tissue with visualization through the transparent tip of the single optical trocar until the transparent tip of the single optical trocar is placed adjacent to the tumor;
    insufflating gas via one of the working channels of the single optical trocar under a positive pressure, wherein the insufflating gas presses against the breast tissue, pressing the breast tissue away to create a cavity in an operative field next to the tumor;
    within the cavity created next to the tumor, dissecting the tumor free with a surgical instrument inserted through one of the working channels;
    removing the tumor through one of the working channels of the single optical trocar;
    wherein the inserting, guiding, insufflating, dissecting and removing are all performed with the single optical trocar such that the single optical trocar is the only trocar used; and
    inserting a dilatation balloon through one of the working channels to create an initial cavity for insufflating gas.

2. The method of claim 1, wherein the single optical trocar comprises an optical trocar member and a trocar sleeve.

3. The method of claim 2, wherein after guiding the transparent tip of the single optical trocar through breast tissue with visualization such that the transparent tip of the single optical trocar is placed adjacent to the tumor, withdrawing the optical trocar member from the trocar sleeve and inserting an endoscopic optics unit.

4. The method of claim 2, wherein one of the working channels is located in the trocar sleeve.

5. The method of claim 1, wherein one of the working channels is an insufflation channel.

6. The method of claim 2, wherein the working channel is an insufflation channel and wherein the insufflation channel is located in the trocar sleeve.

7. The method of claim 1, wherein the skin incision is a periareolar incision.

8. The method of claim 1, wherein guiding the transparent tip of the single optical trocar through breast tissue with visualization includes using wire marking.

9. The method of claim 1, further comprising inserting a morcellator for breaking up the tumor through the trocar sleeve or one of the working channels of the single optical trocar.

10. The method of claim 1, further comprising ultrasonically guiding the transparent tip of the single optical trocar.

\* \* \* \* \*